(12) United States Patent
Gagnon

(10) Patent No.: US 8,911,992 B2
(45) Date of Patent: Dec. 16, 2014

(54) DNA REMOVAL IN TARGET MOLECULE PURIFICATION

(75) Inventor: Peter S. Gagnon, Singapore (SG)

(73) Assignee: Bio-Rad Laboratories, Inc., Hercules, CA (US)

( * ) Notice: Subject to any disclaimer, the term of this patent is extended or adjusted under 35 U.S.C. 154(b) by 128 days.

(21) Appl. No.: 13/096,699

(22) Filed: Apr. 28, 2011

(65) Prior Publication Data

US 2012/0276623 A1 Nov. 1, 2012

(51) Int. Cl.

| | |
|---|---|
| *C07K 1/36* | (2006.01) |
| *C07K 1/20* | (2006.01) |
| *C07K 1/18* | (2006.01) |
| *C07K 1/16* | (2006.01) |
| *C12N 15/10* | (2006.01) |

(52) U.S. Cl.
CPC ............... *C12N 15/101* (2013.01); *C07K 1/18* (2013.01); *C07K 1/165* (2013.01); *C07K 1/36* (2013.01); *C07K 1/20* (2013.01)
USPC ................... 435/320.1; 530/387.1; 530/413; 530/416; 536/25.4

(58) Field of Classification Search
CPC .................................................. C12N 15/101
See application file for complete search history.

(56) References Cited

U.S. PATENT DOCUMENTS

| | | | |
|---|---|---|---|
| 6,504,021 B2 | 1/2003 | Kristyanne et al. | |
| 2009/0186396 A1* | 7/2009 | Gagnon | ..................... 435/235.1 |
| 2011/0002935 A1 | 1/2011 | Wan | |

FOREIGN PATENT DOCUMENTS

WO WO2008/145351 * 12/2008 ............. C07K 16/00

OTHER PUBLICATIONS

Zakharov et al (Inorganic Materials. 2005; 41(5): 509-515).*
Lemmens et al (Journal of Chromatography B. 2003; 784: 291-300).*
Johnson et al (Analytical Biochemistry. 1983; 132: 20-25).*
Jiang et al (Protein Expression and Purification. 2011 (available online Nov. 11, 2010); 7-14).*
Liu et al. (Journal of Chromatography A. [available online Aug. 12, 2011]. 1218: 6943-6952).*
Hans Hjelm (Scandanavian Journal of Immunology. 1975; 4(6): 633-640).*
Gagnon et al. (J. Chromatogr. A 2014; 1340: 68-78).*
Lindhofer et al. (The Journal of Immunology. 1995; 155: 219-225).*
Kelley et al (Biotechnol. Bioeng. 2008;101: 553-566.).*
Peterson et al (Chromatography of Proteins. I. Cellulose Ion-exchange Adsorbents. 1956; 78(4): 751-755).*
International Search Report and Written Opinion from PCT/US2012/035272, dated Jul. 2, 2012.
Gagnon, P.; "Chromatographic behavior of IgM:DNA complexes"; J. Chromatog. A; 1218:2405-2412 (Dec. 2011).
Gagnon, P.; "Dissociation of Antibody-Contaminant Complexes with hydroxyapatile"; *Bioprocessing Journal*; 9:14-24 (Feb. 2011).
Jansson et al.; "Antibody Purification Handbook" Amersham Biosciences. Edition AC. Jan. 17, 2003 retrieved from the Internet on (Junl. 6, 2012) <URK: http://kirschner.med.harvard.edu/files/protocols/GE_antibodypurification.pdf>.
Liu et al.; "Exploration of overlaoded cation exchange chromatography for monoclonal antibody purification"; *J. Chromatog. A*; 1218:6943-6952 (Aug. 2011).

* cited by examiner

*Primary Examiner* — Scott Long
(74) *Attorney, Agent, or Firm* — Kilpatrick Townsend and Stockton LLP

(57) ABSTRACT

Removal of genomic DNA from biological samples using cation exchange is described.

23 Claims, No Drawings

US 8,911,992 B2

DNA REMOVAL IN TARGET MOLECULE PURIFICATION

BACKGROUND OF THE INVENTION

DNA is a contaminant of process solutions and a potential contaminant of purified biotechnology products including therapeutic proteins and vaccines. Regulatory agencies worldwide specify low DNA levels to ensure adequate patient safety. It has also become apparent that contaminating DNA is an impediment to the efficiency of bioprocessing operations, including filtration and purification. It has been suggested recently that DNA may also be responsible for the formation of product aggregates (Gagnon, 2010, Bioprocessing Journal, 9(2) 14-24). Aggregates severely complicate purification and, if not removed, can threaten the safety of patients receiving therapy.

Current methods for DNA reduction focus on anion exchange materials and variants thereof, where DNA is bound by its negative charges to the positively charged anion exchanger. However this method has no utility when the DNA exists in a process solution containing a product that also binds to anion exchangers because the product is removed along with the DNA. Anion exchange-based removal methods are also precluded from application with live cell cultures because anion exchange resins bind cells. A variant of this approach involves DNA removal with hydroxyatite, but this approach has the same limitations as anion exchange. Alternatively, DNA levels may be reduced by the application of nuclease enzymes such as benzonase. However, nuclease-based methods can suffer from high expense. Indeed, small DNA fragments are in some cases more difficult to remove than relatively intact DNA. Nuclease enzymes are also incompatible with live cultures.

BRIEF SUMMARY OF THE INVENTION

The present invention provides for methods of removing genomic DNA from a biological sample comprising a target molecule. In some embodiments, the method comprises contacting the sample to a cation exchange ligand under conditions such that: (a) positively charged complexes comprising genomic DNA from the sample bind the cation exchange ligand; and (b) the target molecule does not substantially bind to the cation exchange ligand; and separating the sample from the positively-charged complexes bound to the cation exchange ligand to produce a sample having a reduced amount of genomic DNA. In some embodiments, the method further comprises, after the separating, performing at least one more target molecule purification step on the sample having a reduced amount of genomic DNA.

In some embodiments, the target molecule is a protein. In some embodiments, the protein is a heterologous protein expressed in a cell. In some embodiments, the protein is an antibody. In some embodiments, the antibody is selected from an IgG and an IgM antibody.

In some embodiments, the target molecule is a nucleic acid. In some embodiments, the nucleic acid is a plasmid.

In some embodiments, the cation exchange ligand comprises a carboxylic acid moiety, or a sulfonic acid moiety, or a phosphoric acid moiety.

In some embodiments, the cation exchange ligand is bound to a solid support. In some embodiments, the solid support is a chromatography column. In some embodiments, the solid support is a bead or particle.

In some embodiments, the cation exchange ligand is bound to a soluble polymer. In some embodiments, soluble polymer comprises carboxymethyl cellulose or dextran sulfate and/or is a phosphorylated polymer.

In some embodiments, the biological sample is a cell culture supernatant.

In some embodiments, the cell culture is selected from the group consisting of a mammalian cell culture, a bacterial cell culture, a yeast cell culture, and an insect cell culture.

In some embodiments, the biological sample is a cell culture. In some embodiments, the cation exchange ligand is linked to a bead or a particle and wherein the presence of the beads or particles in the cell culture reduces aggregation of target molecules. In some embodiments, cells in the cell culture secrete the target molecule.

In some embodiments, the method further comprises, either before or after the contacting, contacting the sample to an anion exchange ligand under conditions such that:
(a) negatively-charged DNA from the sample binds the anion exchange ligand; and
(b) the target molecule does not substantially bind to the anion exchange ligand, thereby separating the target molecule from negatively-charged DNA in the sample.

In some embodiments, the target molecule purification step comprises contacting the sample having a reduced amount of genomic DNA to a cation exchange ligand, an anion exchange ligand, a mixed-mode ligand, an affinity agent, or hydrophobic ligand. In some embodiments, the target molecule purification step comprises contacting the sample with reduced genomic DNA to a cation exchange ligand, an anion exchange ligand, a mixed-mode ligand, an affinity agent, or hydrophobic ligand such that the target molecule binds the ligand or agent; washing other components of the sample from the ligand; and eluting the target molecule from the ligand or agent. In some embodiments, the target molecule purification step comprises contacting the sample having a reduced amount of genomic DNA to a cation exchange ligand, an anion exchange ligand, a mixed-mode ligand, an affinity agent, or hydrophobic ligand in flow-through mode such that the target molecule does not substantially bind to the ligand or agent while another component of the sample binds to the agent or ligand.

DEFINITIONS

"Ion exchange" material has the ability to exchange non-covalently bound counter ions for similarly charged ions of the surrounding solution. Depending on the charge of its exchangeable counter ions the "ion exchange ligand" is referred to as a cation exchange ligand or as an anion exchange ligand. While cation exchange materials can include mixed mode (i.e. mixtures of anion and cation exchangers) materials, in some embodiments, "cation exchange" resins refer to resins or other materials that have cation exchange ligands but not anion exchange ligands. Similarly, while anion exchange resins can include mixed mode (i.e. mixtures of anion and cation exchangers), in some embodiments, "anion exchange" resins refer to resins or other materials that have anion exchange ligands but not cation exchange ligands. An "ion exchange ligand" refers to the chemical moiety of an ion exchange material that exchanges non-covalently bound counter ions. In some embodiments, the ion exchange ligand is immobilized to high molecular weight matrices that carry covalently-bound charged substituents that are used as stationary phase in ion exchange chromatography. Alternatively, the ion exchange ligand can be linked to mobile beads or particles. The beads or particles can be soluble or insoluble in aqueous solutions as desired. In some embodiment, the cation exchanger can comprise negative charges immobilized on a solid phase such as particles, membranes, or monoliths; or can comprise negative charges on a natural or synthetic soluble polymer.

"Antibody" refers to an immunoglobulin, conjugate, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Aggregate" refers to an association of at least two, and often more (e.g., 5, 10, 20 or more) molecules. The association may be either covalent or non-covalent without respect to the mechanism by which the molecules are associated. The association may be direct between the molecules or indirect through other molecules that link the antibodies together. In some embodiments, aggregated molecules include aggregated target molecules. For example, in some embodiments, aggregates include aggregate antibodies. In some embodiments, the aggregates are nucleated at least in part by DNA in the sample.

"Positively-charged protein-DNA complexes" refers to an association of genomic DNA with one or more positively-charged proteins. Examples of positively-charged proteins can include, but are not limited to, histones or other chromosomal proteins.

A "solid support" refers to a material or group of materials having a rigid or semi-rigid surface or surfaces. In some embodiments, the solid support takes the form of thin films or membranes, beads, fibers, woven fibers, shaped polymers, particles, and microparticles, including but not limited to, microspheres. A solid support can be formed, for example, from an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Some exemplary functional groups include, e.g., carboxylic acid (—COOH). In some embodiments, the solid support is a cationic magnetic microsphere.

A "soluble polymer" refers to a polymer that is soluble in aqueous solution. Exemplary polymers can comprise, for example, carboxymethyl-cellulose, dextran sulfate, chondroitin sulfate, heparin sulfate. In some embodiments, the soluble polymer comprises a synthetic water-soluble cationic polymer, e.g., polyacrylic/methacrylic acid, polyphosphoric acid, polyvinylsulfonic acid. In some embodiments, the soluble polymer comprises carboxylated latex.

"Bind-elute mode" refers to an operational approach to chromatography in which the buffer conditions are established so that target molecules and, optionally undesired contaminants, bind to the ionic exchange ligand when the sample is applied to the ligand (which is optionally bound to a solid support). Fractionation of the target can be achieved subsequently by changing the conditions such that the target is eluted from the support. In some embodiments, contaminants remain bound following target elution. In some embodiments, contaminants either flow-through or are bound and eluted before elution of the target.

"Flow-through mode" refers to an operational approach to chromatography in which the buffer conditions are established so that the target molecule to be purified flows through the chromatography support comprising the ion exchange ligand, while at least some sample contaminants are selectively retained, thus achieving their removal.

A "heterologous" protein, when used in the context of a cell, refers to a protein that is not naturally expressed by the cell. For example, a cell recombinantly engineered to express a protein expresses a heterologous protein.

DETAILED DESCRIPTION OF THE INVENTION

I. Introduction

It has been surprisingly discovered that cation exchange chromatography resins are useful for removal of genomic DNA contaminants in biological samples. The use of cation chromatography to remove genomic DNA is counter intuitive in view of DNA's negative charge and the previous use of anion exchange to remove DNA from samples. However, it has been discovered that in some situations anion exchange is not sufficient or available for adequate removal of DNA from the purification target. It is believed that genomic DNA is not completely removed by anion exchange resins in some situations because DNA/chromatin complexes have a positive charge due to positively-charged chromatin proteins (e.g., histones) bound to the DNA.

The present invention provides for removal of positively-charged genomic DNA/protein complexes from biological samples, thereby allowing for purification of a target molecule in the biological sample. At least two formats of this method are contemplated. In one format, the cation exchange ligand is immobilized on a chromatography column or similar format to which the sample is contacted under conditions such that positively-charged genomic DNA/protein complexes bind to the resin while other components of the biological sample, including the target molecule, flow through. In a second format, the cation exchange solid phase is added to a sample (including but not limited to, a cell culture or cell culture supernatant) and incubated with the sample to bind and remove positively-charged genomic DNA/protein complexes from the sample. In the case of cell cultures, positively-charged genomic DNA/protein complexes from lysed cells are bound by the cation exchange solid phase. This second format can be useful, for example, for preventing aggregation of the cells and/or target molecules expressed by the cells.

II. Biological Samples

Biological samples can include any sample from a biological source. Biological samples encompass a variety of sample types obtained from an organism. The term encompasses urine, urine sediment, blood, saliva, and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, sedimentation, or enrichment for certain components. The term encompasses includes cells in cell culture, cell supernatants, cell lysates, serum, plasma, biological fluids, and tissue samples, as well clinical samples.

In some embodiments, the biological sample is a cell culture or a cell culture lysate or filtrate. Any type of cell cultures are contemplated, including but not limited to, non-mammalian animal cell (e.g., avian, e.g., chicken) cultures, mammalian (e.g., human, mouse, rat, goat, bovine, etc.) cell cultures, bacterial cell cultures, a yeast cell cultures, and an insect cell cultures, etc. In some embodiments, the cells have been recombinantly manipulated to express the target molecule. In such embodiments, the target molecule can be secreted from the cell or can accumulate in the cell. Methods for recombinant manipulation of cells and other molecular biology methods are described in, e.g., Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 2002-2011).

Samples contacted to the cation exchange ligands as described herein can be crude samples or can be at least partially purified. Partially purified preparations can come from unpurified preparations that have been processed by at least one chromatography, precipitation, other fractionation step, or any combination of the foregoing. The chromatography step or steps can employ any method, including but not limited to affinity, anion exchange, protein A affinity, hydrophobic interaction, immobilized metal affinity, or mixed-mode chromatography. The precipitation step or steps can include any method including, but not limited to, salt or PEG precipitation. Other fractionation steps can include, but are not limited to, crystallization or membrane filtration.

III. Target Molecules

Target molecules are molecules to be purified in a sample. Different levels of purification of target molecules can be achieved as desired. It is believed that essentially any target molecule in a sample can be purified by the method described herein. Generally, the target molecule either does not bind to the cation exchange ligand used, or is sufficiently prevented from binding to the cation exchange ligand due to competitive binding of positively-charged complexes of proteins and genomic DNA. In some embodiments, the target molecule would bind to an anion exchange ligand, if contacted, thereby preventing efficient removal of DNA using anion exchange. Examples of target molecules, include, e.g., proteins, carbohydrates, lipids, or nucleic acids.

Protein (antibody or non-antibody protein) preparations to which the invention can be applied can include, but are not limited to, unpurified or partially purified proteins (including, e.g., antibodies) from natural, synthetic, or recombinant sources. Exemplary proteins include any protein with a therapeutic, industrial, diagnostic, or other effect. Such proteins can be naturally-occurring or recombinant. The proteins can be generated in tissue or cell cultures or isolated from animals or plants. Unpurified protein preparations can come from various sources including, but not limited to, plasma, serum, ascites, milk, plant extracts, bacterial lysates, yeast lysates, or conditioned cell culture media. The proteins (including but not limited to antibodies) can be PEGylated or alternatively, not PEGylated. Antibodies can include, e.g., IgG, IgM, or other types of antibodies and/or can be fragments or conjugates thereof.

Exemplary nucleic acids to be purified are generally non-genomic DNA nucleic acids or otherwise not in a complex with positively-charged chromosomal proteins, and can include, for example, RNA, plasmids, oligonucleotides, aptamers, super-coiled DNA, linear DNA and single or double-stranded DNA.

IV. Cation Exchangers

The invention provides for contacting a sample to a cation exchanger, i.e., a cation exchange ligand, such that positively-charged protein-DNA complexes are bound to the cation exchanger while at least some other components of the sample, including the target molecule are not bound and can thus be separated from the positively-charged protein-DNA complexes.

The cation exchangers are negatively charged moieties (e.g., cation exchange ligands), and can be immobilized on a soluble or insoluble solid phase such as particles, membranes, or monoliths; or can be negative charged moieties on a natural or synthetic soluble polymer. In some embodiments, the cation exchange groups may also be combined with one or more hydrophobic, hydrogen bonding, anion exchange, or other functionalities, while in other embodiments, cation exchange groups are not so combined.

Exemplary cation exchange ligands include, but are not limited to, e.g., sulfonic acid, sulfopropyl, or carboxymethyl moieties. Depending on the chemical nature of the charged group/substituent the "ion exchange ligand" can also be classified as a strong or weak ion exchange ligand, depending on the strength of the covalently bound charged substituent. For example, in some embodiments, strong cation exchange resins have a sulfonic acid group, e.g., a sulfoalkyl group, e.g., sulfomethyl, sulfoethyl, sulfopropyl, etc., as the charged substituent. Exemplary weak cation exchange resins include those having carboxylic acid group (e.g., a carboxyalkyl group, e.g., carboxymethyl, carboxyethyl, carboxypropyl, etc.) and those having a phosphoric acid group as the charged substituent.

Different types of cation exchange materials, i.e., stationary phases, are available under different names and from a multitude of companies such as e.g., cation exchange materials Bio-Rex® (e.g., type 70), Chelex® (e.g., type 100), Macro-Prep® (e.g., type CM, High S, 25 S), AG® (e.g., type 50W, MP) all available from Bio-Rad Laboratories, Dowex® MAC-3 or Dowex® Wx8 available from Dow chemical company, Mustang C and Mustang S available from Pall Corporation, Cellulose CM (e.g., type 23, 52), hyper-D, partisphere available from Whatman plc., Amberlite® IRC (e.g., type 76, 747, 748), Amberlite® GT 73, Toyopearl® (e.g., type SP, CM, 650M) all available from Tosoh Bioscience GmbH, CM 1500 and CM 3000 available from BioChrom Labs, SP-Sepharose™, CM-Sepharose™ available from GE Healthcare, Poros resins available from PerSeptive Biosystems, Asahipak ES (e.g., type 502C), CXpak P, IEC CM (e.g., type 825, 2825, 5025, LG), IEC SP (e.g., type 420N, 825), IEC QA (e.g., type LG, 825) available from Shoko America Inc., 50W cation exchange resin available from Eichrom Technologies Inc. Other cation exchange ligands and resins are also described in, e.g., US Patent Application No. 2004/0137419.

General chromatographic methods and their use are known to a person skilled in the art. See for example, Chromatography, 5th edition, Part A: Fundamentals and Techniques, Heftmann (ed) Elsevier Science Publishing Company 1992 Chromatography 5th ed 51 A 1992; Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991);

Scopes, Protein Purification: Principles and Practice (1982); Sambrook, J., et al. (ed), Molecular Cloning: A Laboratory Manual, Second Edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

The biological sample can be applied to the cation exchange ligand under any conditions that allow for binding of positively-charged protein-DNA complexes to the ligand while the target molecule does not substantially bind to the ligand. In some embodiments, the sample requires no alteration and can be simply applied to the cation exchange ligand (e.g., immobilized on a column) and non-binding components of the sample, including the target molecule, can then be separated from the cation exchange ligand bound to the positively-charged protein-DNA complexes. In some embodiment, especially in which the target has low or no attraction to the cation exchange ligand, the sample can be diluted (e.g., with water), reducing salt concentrations. In some embodiments, dilution will increase the ability of the cation exchange ligand to bind the positively-charged protein-DNA complexes and/or remove other contaminants. In embodiments in which the target has a slight to moderate attraction to a cation exchanger (e.g., less than the attraction of the positively-charged protein-DNA complexes for the cation exchange ligand) salts can be added to the sample, thereby blocking binding of the target to the cation exchanger while still allowing for binding of the positively-charged protein-DNA complexes to the cation exchanger. As noted in the examples, it has been found that at least 3M guanidine removes the positively-charged protein-DNA complexes from cation exchangers.

Generally, it is expected that no effort will be made to remove the positively-charged protein-DNA complexes from the cation exchanger. Instead, it is expected that in most embodiments, the cation exchanger, with positively-charged protein-DNA complexes bound, will simply be discarded. However, as desired, the positively-charged protein-DNA complexes can be removed, for example, with 3 M guanidine or other high salt solutions.

V. Cation Exchange Formats

The cation exchange ligands can be presented to the sample in a number of different formats to remove positively charged protein-DNA complexes. For example, in some embodiments, the cation exchange ligands are linked to a chromatography resin, which is, for example, in a packed column, a packed bed column, a fluidized/expanded bed column, and/or as part of a batch operation. The cation exchange resin can be packed in a column of any dimension required to remove the positively-charged protein/DNA complexes. Column diameter may range, for example, from less than 1 cm to more than 1 meter, and column height may range from less than 1 cm to more than 30 cm depending on the requirements of a particular application. It will be appreciated that the present invention is not limited to the above heights and diameters. Appropriate column dimensions can be determined by the skilled artisan.

In steps where removal of the positively-charged protein-DNA complexes is desired, the cation exchange chromatography is operated in "flow-through" mode, i.e., such that the target molecule does not substantially bind to the cation exchange ligands. "Does not substantially bind" means, for example that at least a majority (e.g., at least 60%, 70%, 80%, 90%, or 95%) of target molecules flow through the cation exchange ligands and are separated from bound material. As noted in the Examples, in embodiments where the target molecule (e.g., IgM) would bind the cation exchange ligand in the absence of the positively-charged protein-DNA complexes, once the positively-charged protein-DNA complexes have been removed, the sample can subsequently be applied to a second cation exchange step in "bind-elute" mode, thereby binding the target molecule to the cation exchange ligand, washing other components of the sample from the ligand, and then eluting the target molecule.

In some embodiments, the samples can be contacted to, and mixed with, beads or other solid particles linked to the cation exchange ligand, thereby binding positively-charged protein-DNA complexes in the sample to the ligands. The beads or particles bound to the positively-charged protein-DNA complexes can then be removed, thereby removing positively-charged protein-DNA complexes from the sample. Removal of the beads or particles can include, for example, centrifugation, filtration, magnetic removal, or other forms of physical removal as appropriate.

In some embodiments, the samples can be contacted to, and mixed with, soluble polymers linked to the cation exchange ligand, thereby binding positively-charged protein-DNA complexes in the sample to the ligands. Exemplary soluble particles can be formulated with, e.g., carboxymethyl-cellulose, dextran sulfate, chondroitin sulfate, heparin sulfate or synthetic water-soluble cationic polymers, e.g., polyacrylic/methacrylic acid, polyphosphoric acid, polyvinylsulfonic acid. Generally, the interaction of the cation exchange ligands linked to the soluble polymers and the positively-charged protein-DNA complexes will result in a precipitate that can be readily removed (e.g., by centrifugation or other techniques) from the remaining soluble parts of the sample.

In some embodiments, the solid beads or particles or soluble polymers (linked to the cation exchange ligand) are added to a sample containing cells. The sample can be, for example, an active cell culture or a culture upon termination of active culture conditions. For the active culture option (e.g., when cells are dividing and production of target molecules by the cells is increasing), the beads, particles, or soluble polymers can be added directly to the cell culture, thereby allowing for any positively-charged protein-DNA complexes in the culture to bind to the cation exchange ligands.

It is believed DNA in cultures (e.g., released from dead or lysed cells) can act as points of aggregation of other molecules, including but not limited to antibodies or other proteins. Sequestration of DNA from active cultures onto cation exchange ligands on beads or particles offers potential for preventing antibody (or other target cell product) aggregate formation otherwise caused by nucleation around DNA. The beads or particles can be left in the cultures until the cells are harvested, or alternatively can be removed (e.g., continuously or batch-wise) during cell culture. For continuous culture, the beads and particles can be added and removed in a continuous or batchwise manner.

Cell cultures can include cells naturally-expressing or -producing a target molecule or cells that recombinantly- or otherwise-engineered to express or produce the target molecule. In some embodiments, the cells secrete the target molecule, e.g., into the supernatant. It is believed any type of cell cultures can be used with the cation-exchange ligands of the invention, including but not limited to, mammalian, insect, fungal, yeast, or bacterial cell cultures. In some embodiments, the target molecule produced by the cells is an antibody or other (e.g., therapeutic) protein.

VI. Further Purification of the Target Molecule

Prior to, or after, removal of positively-charged protein-DNA complexes from the sample, the target molecule in the sample can be further purified. Examples of further purification methods include but are not limited to affinity chromatography (e.g., such as protein A affinity chromatography for purification of antibodies), anion exchange chromatography, cation exchange chromatography, hydrophobic interaction chromatography, immobilized metal affinity chromatography, mixed mode chromatography, precipitation, filtration, crystallization, or phase partitioning.

In some embodiments, positively-charged protein-DNA complexes are removed from the same using cation exchange, as described herein, and negatively charged polynucleotides (e.g., DNA) are removed using anion exchange. In this option, the sample is applied to an anion exchange ligand such that the negatively charged polynucleotides bind the anion exchanger whereas the target molecule flows through or otherwise does not significantly bind to the anion exchanger. The anion exchange step can occur before (e.g., immediately before) or after (e.g., immediately after) the cation exchange step.

EXAMPLE

Example 1

The following example describes removal of DNA from a preparation of monoclonal IgM. DNA was present at high levels in the cell culture supernatant due to high cell mortality at the time of harvest. The presence of the DNA precluded efficient capture of IgM by either anion exchange or hydroxypatite chromatography because DNA bound more strongly to the anion exchange ligand and hydroxypatite than the IgM and thus consumed most of the available binding capacity.

IgM capture by cation exchange was precluded because the particular target IgM was inadequately retained by cation exchangers. The IgM was captured on a hydrophobic/cation exchange mixed mode, but this attempt unexpectedly suffered from the same problem as anion exchange and hydroxypatite: DNA bound more strongly than IgM and consumed most of the binding capacity. Analysis revealed that the DNA was complexed with protein. In a separate experiment, filtered cell supernatant was applied to a solid-phase cation exchanger (Dowex Wx8) packed in a column. The cell culture was not diluted and the pH was not modified. IgM passed through the exchanger, while DNA was selectively capture and removed. The DNA was subsequently removed from the cation exchanger by treatment with 3 M guanidine, pH ~5. The treated (flow-through) supernatant, now significantly lacking DNA, was then diluted, the pH was adjusted, and it was applied to the hydrophobic/cation exchanger mixed mode chromatography column. The IgM bound, without encumberment by DNA. Application to anion exchange or hydroxypatite would have been similarly enabled. This application s highlights the value of the invention for proteins with properties that preclude DNA removal by anion exchange methods.

Example 2

This example demonstrates that the solid phase cation exchanger can be added directly to cell culture supernatant in bulk, incubated for a suitable period of time, and can then be removed with the bound DNA by filtration. Specifically, Dowex 50WX8 2-00-400 mesh, pre-equilibrated with phosphate buffered saline, was added to to cell culture supernatant (physiological conditions) at a volumetric ratio. of 2% Dowex. The mixture was stirred overnight in the cold. The mixture was then filtered through a 0.22 micron filter to remove the Dowex and bound DNA.

It is also believed that the mixture could also have been co-precipitated with a soluble cation exchanger (e.g., a cation exchange ligand linked to a soluble polymer), then removed by filtration or centrifugation.

Example 3

The following hypothetical example describes application to IgG monoclonal antibodies to a cation exchange column to remove positively-charged DNA complexes. Cell supernatants containing monoclonal IgG are commonly treated with anion exchange materials to reduce DNA content. Most IgG monoclonal antibodies are not bound by cation exchangers under physiological conditions. Cell supernatants are contacted to a cation exchange ligand (e.g., in a chromatography column) under conditions in which the positively-charged DNA complexes bind the cation exchange ligand and the target IgG flows through the column. Optionally, the mixture can also be applied in conjunction with anion exchangers, i.e., either before or after the cation exchange step, thereby removing both positively-charged complexes and negatively charged nucleic acids.

Example 4

The following hypothetical example describes application to antibody-containing active mammalian or non-mammalian (e.g., bacterial, yeast, etc.) cell cultures. Cation-exchange ligands linked to beads are applied to live cell cultures to dynamically remove DNA as it is expelled by dying cells. Because cells are negatively charged, they are repelled by the cation exchanger, and are unimpaired. In contrast, positively-charged DNA in the culture (e.g., from lysed or dead cells) are bound by the cation exchange ligand. Sequestration of DNA from active cultures offers potential for preventing antibody (or other target cell product) aggregate formation otherwise caused by nucleation around DNA.

Alternatively, the cation exchange ligand linked to beads is applied immediately upon termination of cell culture production (prior to, or after, cell removal).

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

What is claimed is:

1. A method of removing genomic DNA from a cell culture biological sample or culture supernatant biological sample comprising a protein target molecule and positively charged complexes comprising genomic DNA, the method comprising, contacting the cell culture biological sample or culture supernatant biological sample to a cation exchange ligand comprising as a charged substituent a sulfonic acid or phosphoric acid moiety, said ligand bound to a solid support or bound to a soluble polymer under conditions such that:
(a) positively charged genomic complexes comprising DNA from the sample bind the cation exchange ligand; and
(b) non-binding components of the sample, including the protein target molecule, do not substantially bind to the cation exchange ligand, the solid support, or the soluble polymer;

separating the non-binding components of the sample, including the target molecule, from the positively-charged complexes bound to the cation exchange ligand to produce a purified sample having a reduced amount of genomic DNA; and performing at least one more protein target molecule purification step on the purified sample having a reduced amount of genomic DNA, wherein the protein target does not bind the cation exchange ligand from the contacting through the separating.

2. The method of claim 1, wherein the protein target molecule is a heterologous protein expressed in a cell.

3. The method of claim 1, wherein the protein target molecule is an antibody.

4. The method of claim 3, wherein the antibody is selected from an IgG and an IgM antibody.

5. The method of claim 1, wherein the cation exchange ligand is bound to a solid support.

6. The method of claim 5, wherein the solid support is a chromatography column.

7. The method of claim 5, wherein the solid support is a bead or particle.

8. The method of claim 1, wherein the cation exchange ligand is bound to a soluble polymer.

9. The method of claim 8, wherein soluble polymer comprises carboxymethyl cellulose or dextran sulfate.

10. The method of claim 1, wherein the biological sample is from a cell culture.

11. The method of claim 10, wherein the biological sample is a cell culture supernatant.

12. The method of claim 11, wherein the cell culture is selected from the group consisting of a mammalian cell culture, a bacterial cell culture, a yeast cell culture, and an insect cell culture.

13. The method of claim 1, wherein the biological sample is a cell culture.

14. The method of claim 13, wherein the cation exchange ligand is linked to a bead or a particle and wherein the presence of the beads or particles in the cell culture reduces aggregation of target molecules.

15. The method of claim 13, wherein cells in the cell culture secrete the protein target molecule.

16. The method of claim 1, further comprising, either before or after the contacting, contacting the sample to an anion exchange ligand under conditions such that:
(a) negatively-charged DNA from the sample binds the anion exchange ligand; and
(b) the protein target molecule does not substantially bind to the anion exchange ligand, thereby separating the protein target molecule from negatively-charged DNA.

17. The method of claim 1, wherein the protein target molecule purification step comprises contacting the sample having a reduced amount of genomic DNA to a cation exchange ligand, an anion exchange ligand, a mixed-mode ligand, an affinity agent, or hydrophobic ligand.

18. The method of claim 17, wherein the protein target molecule purification step comprises contacting the sample with reduced genomic DNA to a cation exchange ligand, an anion exchange ligand, a mixed-mode ligand, an affinity agent, or hydrophobic ligand such that the protein target molecule binds the ligand or agent;
washing other components of the sample from the ligand; and
eluting the protein target molecule from the ligand or agent.

19. The method of claim 17, wherein the protein target molecule purification step comprises contacting the sample having a reduced amount of genomic DNA to a cation exchange ligand, an anion exchange ligand, a mixed-mode ligand, an affinity agent, or hydrophobic ligand in flow-through mode such that the protein target molecule does not substantially bind to the ligand or agent while another component of the sample binds to the agent or ligand.

20. The method of claim 1, wherein the cation exchange ligand comprises a phosphoric acid moiety as a charged substituent.

21. The method of claim 1, wherein the solid support or solid polymer does not have an anion exchange ligand.

22. The method of claim 1, wherein the cation exchange ligand comprises a sulfonic acid moiety as a charged substituent.

23. The method of claim 4, wherein the target molecule is an IgM and the IgM is subsequently purified following removal of the positively charged genomic complexes.

* * * * *